United States Patent
White

(10) Patent No.: US 6,846,476 B2
(45) Date of Patent: Jan. 25, 2005

(54) TREATMENT OF B-CELL ASSOCIATED DISEASES

(75) Inventor: Christine White, Rancho Santa Fe, CA (US)

(73) Assignee: IDEC Pharmaceuticals Corporation, San Diego, CA (US)

( * ) Notice: Subject to any disclaimer, the term of this patent is extended or adjusted under 35 U.S.C. 154(b) by 190 days.

(21) Appl. No.: 09/883,962

(22) Filed: Jun. 20, 2001

(65) Prior Publication Data

US 2002/0039557 A1 Apr. 4, 2002

Related U.S. Application Data

(60) Provisional application No. 60/212,668, filed on Jun. 20, 2000.

(51) Int. Cl.$^7$ .............................................. A61K 51/00
(52) U.S. Cl. .................................... 424/1.49; 424/1.69
(58) Field of Search .............................. 424/1.49, 1.53, 424/1.69, 144.1, 143.1, 154.1, 141.1, 130.1, 133.1, 134.1, 136.1, 138.1, 174.1, 178.1, 181.1, 183.1; 530/391.3

(56) References Cited

U.S. PATENT DOCUMENTS

| | | |
|---|---|---|
| 5,286,850 A | 2/1994 | Gansow |
| 5,789,554 A | 8/1998 | Leung et al. |
| 6,090,365 A | 7/2000 | Kaminski et al. |
| 6,113,898 A | 9/2000 | Anderson |
| 6,183,744 B1 | 2/2001 | Goldenberg |
| 6,306,393 B1 | 10/2001 | Goldenberg |
| 6,410,319 B1 * | 6/2002 | Raubitschek et al. ..... 435/343.1 |
| 6,451,284 B1 | 9/2002 | Raestetter |
| 6,455,043 B1 | 9/2002 | Grillo-López |
| 2002/0006404 A1 | 1/2002 | Hanna |
| 2002/0058029 A1 | 5/2002 | Hanna |

FOREIGN PATENT DOCUMENTS

| | | |
|---|---|---|
| WO | WO 00/67796 | 10/1998 |
| WO | WO 98/42378 | 10/1998 |
| WO | WO 00/20864 | 4/2000 |
| WO | WO 00/74718 | 12/2000 |
| WO | WO 01/10461 | 2/2001 |

OTHER PUBLICATIONS

Maloney et al., Newer Treatments of Non–Hodgkin's Lymphoma: Monoclonal Antibodies, Oncology 1998 vol. 12, No. 8 pp. 63–76.

* cited by examiner

Primary Examiner—Michael G. Hartley
(74) Attorney, Agent, or Firm—Pillsbury Winthrop LLP

(57) ABSTRACT

Treatment of B-cell associated diseases including autoimmune and B-cell malignancies such as leukemias, lymphomas, using the combination of an anti-CD20 antibody, preferably RITUXAN® and a radiolabeled anti-CD22 antibody, preferably an $^{90}$Y labeled humanized anti-CD22 antibody, is described. These therapeutic regimens provide for enhanced depletion of B cells, and therefore reduce the risk in B cell malignancy treatment of relapse associated with RITUXAN® and, moreover, provide for prolonged immunosuppression of B-cell immune responses, especially in the context of autoimmune diseases and transplant.

12 Claims, No Drawings

TREATMENT OF B-CELL ASSOCIATED DISEASES

CROSS REFERENCE TO RELATED APPLICATION

This application claims priority from U.S. Provisional Ser. No. 60/212,668, filed Jun. 20, 2000, and which is incorporated herein in its entirety by reference.

FIELD OF THE INVENTION

The present invention is concerned with a combination immunotherapy/-radiotherapy involving the administration of a cold anti-CD20 antibody, preferably RITUXAN®, or another anti-CD20 antibody having substantially the same B-cell depleting activity as RITUXAN®, and a radiolabeled anti-CD22 antibody, preferably an yttrium labeled humanized anti-CD22 antibody. In the case of tumor therapy, the initial administration of the cold anti-CD23 antibody helps remove B cells from the circulation, thereby improving the targeting and efficacy of the radiolabeled anti-CD22 antibody.

Also, the subject treatment provides for enhanced immunosuppression vis-à-vis cold CD20 and radiolabeled anti-CD22 therapy alone. This combination therapeutic regimen is useful in the treatment of diseases wherein depletion and/or selective killing, and/or blocking the function of CD20 and CD22 expressing cells is therapeutically beneficial, especially B-cell malignancies, lymphomas, leukemias, and conditions or diseases wherein suppression of B-cell immune function is therapeutically beneficial, e.g., autoimmune diseases, allergic diseases, transplant, and other therapeutic regimens involving administration of antigenic moieties, e.g., protein, cell or gene therapy. Preferably, the therapeutic regimen will comprise the initial administration of RITUXAN®, followed by administration of the radiolabeled anti-CD22 antibody.

BACKGROUND OF THE INVENTION

I. Anti-CD20 Antibodies

CD20 is a cell surface antigen expressed on more than 90% of B-cell lymphomas and does not shed or modulate in the neoplastic cells (McLaughlin et al., *J. Clin. Oncol.* 16: 2825–2833 (1998)). Anti-CD20 antibodies have been prepared for use both in research and therapeutics. One reported anti-CD20 antibody is the monoclonal B1 antibody (U.S. Pat. No. 5,843,398). Anti-CD20 antibodies have also been prepared in the form of radionuclides for treating B-cell lymphoma (e.g., $^{131}$I-labeled anti-CD20 antibody), as well as a $^{89}$Sr-labeled form for the palliation of bone pain caused by prostate and breast cancer metastasises (Endo, *Gan To Kagaku Ryoho* 26: 744–748 (1999)).

A murine monoclonal antibody, 1F5, (an anti-CD20 antibody) was reportedly administered by continuous intravenous infusion to B cell lymphoma patients. However, extremely high levels (>2 grams) of 1F5 were reportedly required to deplete circulating tumor cells, and the results were described as "transient" (Press et al., *Blood* 69: 584–591 (1987)). A potential problem with using monoclonal antibodies as therapeutics is that non-human monoclonal antibodies (e.g., murine monoclonal antibodies) typically lack human effector functionality, e.g., they are unable to, inter alia, mediate complement dependent lysis or lyse human target cells through antibody-dependent cellular toxicity or Fc-receptor mediated phagocytosis. Furthermore, non-human monoclonal antibodies can be recognized by the human host as a foreign protein; therefore, repeated injections of such foreign antibodies can lead to the induction of immune responses leading to harmful hypersensitivity reactions. For murine-based monoclonal antibodies, this is often referred to as a Human Anti-Mouse Antibody response, or "HAMA" response. Additionally, these "foreign" antibodies can be attacked by the immune system of the host such that they are, in effect, neutralized before they reach their target site.

A. Rituximab

Rituximab (also known as RITUXAN®, MABTHERA® and IDEC-C2B8) was the first FDA-approved monoclonal antibody and was developed at IDEC Pharmaceuticals (see U.S. Pat. Nos. 5,843,439; 5,776,456 and 5,736,137). Rituximab is a chimeric, anti-CD20 monoclonal (MAb) recommended for treatment of patients with low-grade or follicular B-cell non-Hodgkin's lymphoma (McLaughlin et al., *Oncology (Huntingt)* 12: 1763–1777 (1998); Leget et al., *Curr. Opin. Oncol.* 10: 548–551 (1998)). In Europe, rituximab has been approved for therapy of relapsed stage III/IV follicular lymphoma (White et al., *Pharm. Sci. Technol. Today* 2: 95–101 (1999)). Other disorders treatable with rituximab include follicular centre cell lymphoma (FCC), mantle cell lymphoma (MCL), diffuse large cell lymphoma (DLCL), and small lymphocytic lymphoma/chronic lymphocytic leukemia (SLL/CLL) (Nguyen et al., 1999)). Rituximab has exhibited minimal toxicity and significant therapeutic activity in low-grade non-Hodgkin's lymphomas (NHL) in phase I and II clinical studies (Berinstein et al., *Ann. Oncol.* 9: 995–1001 (1998)).

Rituximab, which is currently being used alone to treat B-cell NHL at weekly doses of typically 375 mg/M$^2$ for four weeks with relapsed or refractory low-grade or follicular NHL. This antibody is well tolerated and had significant clinical activity (Piro et al., *Ann. Oncol.* 10: 655–61 (1999); Nguyen et al., *Eur. J. Haematol.* 62: 76–82 (1999); and Coiffier et al., *Blood* 92: 1927–1932 (1998)). Also, up to 500 mg/M$^2$ of four weekly doses have also been administered during trials using the antibody (Maloney et al., *Blood* 90: 2188–2195 (1997)). Rituximab also has been combined with chemotherapeutics, such as CHOP (e.g., cyclophosphamide, doxorubicin, vincristine and prednisone), to treat patients with low-grade or follicular B-cell non-Hodgkin's lymphoma (Czuczman et al., *J. Clin. Oncol.* 17: 268–76 (1999); and McLaughlin et al., *Oncology (Huntingt)* 12: 1763–1777 (1998)). However, it has not previously been utilized in combination with other therapeutic antibodies.

The synthesis of monoclonal antibodies against CD22 and their use in therapeutic regimens has also been reported. CD22 is a B-cell-specific molecule involved in B-cell adhesion that may function in homotypic or heterotypic interactions (Stamenkovic et al, *Nature* 344:74 (1990); Wilson et al, *J. Exp. Med.* 173:137 (1991); Stamenkovic et al, *Cell* 66:1133 (1991)). The CD22 protein is expressed in the cytoplasm of progenitor B and pre-B-cells (Dorken et al, *J. Immunol.* 136:4470 (1986); Dorken et al, "Expression of cytoplasmic CD22 in B-cell ontogeny. In Leukocyte Typing III, White Cell Differentiation Antigens. McMichael et al, eds., Oxford University Press, Oxford, p. 474 (1987); Schwarting et al, *Blood* 65:974 (1985); Mason et al, *Blood* 69:836 (1987)), but is found only on the surface of mature B-cells, being present at the same time as surface IgD (Dorken et al, *J. Immunol.* 136:4470 (1986)). CD22 expression increases following activation and disappears with further differentiation (Wilson et al, *J. Exp. Med.* 173:137 (1991); Dorken et al, *J. Immunol.* 136:4470 (1986)). In lymphoid tissues, CD22 is expressed by follicular mantle and marginal zone B-cells but only weakly by germinal center B-cells (Dorken et al, *J. Immunol.* 136:4470 (1986); Ling et al, "B-cell and plasma antigens: new and previously defined clusters" In Leukocyte Typing III. White Cell Differentiation Antigens, McMichael et al, eds., Oxford University Press, Oxford, p. 302 (1987)). However, in situ hybridization reveals the strongest expression of CD22 mRNA within the germinal center and weaker expression within the mantle zone (Wilson et al, *J. Exp. Med.* 173:137 (1991)). CD22 is speculated to be involved in the regulation of B-cell activation since the binding of CD22 mAb to B-cells in vitro has been found to augment both the increase in intracellular free calcium and the proliferation induced after cross-linking of surface Ig (Pezzutto et al, *J. Immunol.* 138:98 (1987); Pezzutto et al, *J. Immunol.* 140:1791 (1988)). Other studies have determined, however, that the augmentation of anti-Ig induced proliferation is modest (Dorken et al, *J. Immunol.* 136:4470 (1986)). CD22 is constitutively phosphorylated, but the level of phosphorylation is augmented after treatment of cells with PMA (Boue et al, *J. Immunol.* 140:192 (1988)). Furthermore, a soluble form of CD22 inhibits the CD3-mediated activation of human T-cells, suggesting CD22 may be important in T-cell-B-cell interactions (Stamenkovic et al, *Cell* 66:1133 (1991)).

Ligands that specifically bind the CD22 receptor have been reported to have potential application in the treatment of various diseases, especially B-cell lymphomas and autoimmune diseases. In particular, the use of labeled and non-labeled anti-CD22 antibodies for treatment of such diseases has been reported.

For example, Tedder et al, U.S. Pat. No. 5,484,892, that purportedly bind CD22 with high affinity and block the interaction of CD22 with other ligands. These monoclonal antibodies are disclosed to be useful in treating autoimmune diseases such as glomerulonephritis, Goodpasture's syndrome, necrotizing vasculitis, lymphadenitis, periarteritis nodosa, systemic lupus erythematosis, arthritis, thrombocytopenia purpura, agranulocytosis, autoimmune hemolytic anemias, and for inhibiting immune reactions against foreign antigens such as fetal antigens during pregnancy, myasthenia gravis, insulin-resistant diabetes, Graves' disease and allergic responses.

Also, Leung et al, U.S. Pat. No. 5,789,557, disclose chimeric and humanized anti-CD22 monoclonal antibodies produced by CDR grafting and the use thereof in conjugated and unconjugated form for therapy and diagnosis of B-cell lymphomas and leukemias. The reference discloses especially such antibodies conjugated to cytotoxic agents, such as chemotherapeutic drugs, toxins, heavy metals and radionuclides. (See U.S. Pat. No. 5,789,554, issued Aug. 4, 1998, to Leung et al, and assigned to Immunomedics.)

Further, PCT applications WO 98/42378, WO 00/20864, and WO 98/41641 describe monoclonal antibodies, conjugates and fragments specific to CD22 and therapeutic use thereof, especially for treating B-cell related diseases.

Also, the use of anti-CD22 antibodies for treatment of autoimmune diseases and cancer has been suggested. See, e.g., U.S. Pat. No. 5,443,953, issued Aug. 22, 1995 to Hansen et al and assigned to Immunomedics Inc. that purports to describe anti-CD22 immunoconjugates for diagnosis and therapy, especially for treatment of viral and bacterial infectious diseases, cardiovascular disease, autoimmune diseases, and cancer, and U.S. Pat. No. 5,484,892, issued Jan. 16, 1998 to Tedder et al and assigned to Dana-Farber Cancer institute, Inc. that purports to describe various monoclonal antibodies directed against CD22, for treatment of diseases wherein retardation or blocking of CD22 adhesive function is therapeutically beneficial, particularly autoimmune diseases.) These references suggest that an anti-CD22 antibody of fragment may be directly or indirectly conjugated to a desired effector moiety, e.g., a label that may be detected, such as an enzyme, fluorophore, radionuclide, electron transfer agent during an in vitro immunoassay or in vivo imaging, or a therapeutic effector moiety, e.g., a toxin, drug or radioisotope.

Further, an anti-human CD22 monoclonal antibody of the IgG1 isotype is commercially available from Leinco Technologies, and reportedly is useful for treatment of B-cell lymphomas and leukemias, including hairy cell leukemia. (Campana, D. et al, *J. Immunol.* 134:1524 (1985)). Still further, Dorken et al, *J. Immunol.* 150:4719 (1993) and Engel et al, *J. Immunol.* 150:4519 (1993) both describe monoclonal antibodies specific to CD22.

Also, the combined administration of an anti-CD22 immunotoxin and an anti-CD19 immunotoxin has been reported for the treatment of diseases including cancer and autoimmune diseases. (See U.S. Pat. No. 5,686,072, issued Nov. 11, 1997 to Uhr et al land assigned to The University of Texas.)

Therefore, based on the foregoing, while RITUXAN® and other therapies have been reported for treatment of B-cell lymphomas, often such treatments are subject to relapse. Therefore, notwithstanding what has been reported relating to the use of anti-CD20 antibodies and anti-CD22 antibodies in therapeutic regimens, it would be an advantage if novel therapeutic regimens could be developed, especially combination therapies that provide for enhanced therapeutic efficacy. In particular, it would be advantageous if novel therapies could be developed that prevent or reduce disease relapse in patients treated with RITUXAN® or other anti-CD20 antibody therapeutic regimens.

PREFERRED EMBODIMENTS OF THE INVENTION

It is an embodiment of the invention to provide a novel therapeutic regimen that comprises the administration of an anti-CD20 monoclonal antibody or fragment thereof, and the administration of a radiolabeled anti-CD22 monoclonal antibody or fragment.

It is another embodiment of the invention to provide a novel therapeutic regimen involving the initial administration of RITUXAN®, followed by the administration of a radiolabeled anti-CD22 monoclonal antibody, or fragment thereof.

It is another embodiment of the invention to provide a novel therapeutic regimen for the treatment of B-cell malignancies and cancers, especially B-cell leukemias or lymphomas, comprising the administration of RITUXAN®, followed by a radiolabeled humanized anti-CD22 antibody.

It is another embodiment of the invention to provide novel methods for the treatment of autoimmune diseases and transplant comprising the administration of RITUXAN®, followed by a radiolabeled anti-CD22 antibody.

It is another embodiment of the invention to provide novel methods of inhibiting B-cell immune responses, especially in protein, gene or cell therapy, or in the treatment of allergic disorders by the combined administration of an anti-CD20 antibody and a radiolabeled anti-CD22 antibody.

SUMMARY OF THE INVENTION

The present invention relates to methods of treating patients having diseases wherein inhibiting and/or depleting and/or killing and/or blocking the formation of B-cells is therapeutically desirable, especially B-cell malignancies and leukemias, as well as autoimmune diseases, transplant, allergic disorders, inflammatory disorders and gene or cell therapy, and other conditions wherein B-cell immunity is desirably suppressed. In a preferred embodiment, the present invention relates to the treatment of B-cell lymphomas and leukemias, especially non-Hodgkin's lymphoma (NHL).

Essentially, the subject therapeutic regimen will comprise the administration of a cold anti-CD20 antibody or fragment, and a hot (radiolabeled) anti-CD22 antibody or fragment. The anti-CD20 antibody and the radiolabeled anti-CD22 antibody can be administered in combination or separately, and in either order. Preferably, the anti-CD20 antibody will be administered first, in sufficient amounts to effect B-cell depletion, followed by the administration of a radiolabeled anti-CD22 antibody.

Preferably, this combination will affect synergistic results vis-à-vis the use of the cold anti-CD20 or radiolabeled anti-CD22 antibody or fragment alone. In a particularly preferred embodiment, this combination will provide for enhanced killing or depletion of tumorigenic B cells because the cold anti-CD20 antibody initially clears most CD20 expressing cells and the radiolabeled anti-CD22 antibody clears substantially all remaining tumorigenic B cells. Optionally, the combination therapy may further include the use of a radiolabeled anti-CD20 antibody, e.g. radiolabeled 2B8 (Zevalin®).

In another preferred embodiment, this combination will prevent or inhibit relapse in patients with B cell malignancies, e.g. non-Hodgkin's lymphoma, vis-à-vis current Rituxan®-based therapeutic regimens.

DETAILED DESCRIPTION OF THE INVENTION

In order to clearly describe the invention, the following definitions are provided.

Definitions

Units, prefixes, and symbols can be denoted in their Si accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the invention which can be had by reference to the specification as a whole. Accordingly, the terms defined immediately below are more fully defined by reference to the specification in its entirety.

The term "antibody" as used herein is intended to include immunoglobulins and fragments thereof which are specifically reactive to the designated protein or peptide thereof. An antibody can include human antibodies, primatized antibodies, chimeric antibodies, bispecific antibodies, humanized antibodies, antibodies fused to other proteins or radiolabels, and antibody fragments.

The term "antibody" herein is used in the broadest sense and specifically covers intact monoclonal antibodies, polyclonal antibodies, multispecific antibodies (e.g. bispecific antibodies) formed from at least two intact antibodies, and antibody fragments so long as they exhibit the desired biological activity.

"Antibody fragments" comprise a portion of an intact antibody, preferably comprising the antigen-binding or variable region thereof. Examples of antibody fragments include Fab, Fab', F(ab')2, and Fv fragments; diabodies; linear antibodies; single-chain antibody molecules; and multispecific antibodies formed from antibody fragments. Antibody fragments may be isolated using conventional techniques. For example, F(ab$^1$)$_2$ fragments can be generated by treating antibodies with pepsin. The resulting F(ab$^1$)$_2$ fragment can be treated to reduce disulfide bridges to produce Fab$^1$ fragments.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a 13-sheet configuration, connected by three hypervariable regions, which form loops connecting, and in some cases forming part of, the B-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the VH–VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CHI) of the heavy chain. Fab' fragments differ from Fab fragments by the addition of a few residues at the carboxy terminus of the heavy chain CHI domain including one or more cysteines from the antibody hinge region. Fab'-SH is the designation herein for Fab' in which the cysteine residue(s) of the constant domains bear at least one free thiol group. F(ab')Z antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgGI, IgG2, IgG3, IgG4, IgA, and IgA2. The heavy-chain constant domains that correspond to the different classes of antibodies are called alpha, delta, epsilon, gamma and mu, respectively. Preferably, the heavy-chain constant domains will complete the gamma-1, gamma-2, gamma-3 and gamma-4 constant region. Preferably, these constant domains will also comprise modifications to enhance antibody stability such as the P and E modification disclosed in U.S. Pat. No. 6,011,138 incorporated by reference in its entirety herein. The subunit structures and three dimensional configurations of different classes of immunoglobulins are well known.

"Single-chain Fv" or "scFv" antibody fragments comprise the VH and VL domains of antibody, wherein these domains are present in a single polypeptide chain. Preferably, the Fv polypeptide further comprises a polypeptide linker between the VH and VL domains which enables the scFv to form the desired structure for antigen binding. For a review of scFv see Pluckthun in *The Pharmacology of Monoclonal Antibodies,* vol. 113, Rosenburg and Moore eds., Springer-Verlag, New York, pp. 269–315 (1994).

The term "diabodies" refers to small antibody fragments with two antigen-binding sites, which fragments comprise a heavy-chain variable domain (VH) connected to a light chain variable domain (VL) in the same polypeptide chain (VH–VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al, *Proc. Natl. Acad.* Sci. USA, 90:6444–6448 (1993).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256:495 (1975), or may be made by recombinant DNA methods (see, e.g., U.S. Pat. No. 4,816,567). The "monoclonal antibodies" may also be isolated from phage antibody libraries using the techniques described in Clackson et al, Nature, 352:624–628 (1991) and Marks et al., *J. Mol. Biol.,* 222:581–597 (1991), for example.

By "humanized antibody" is meant an antibody derived from a non-human antibody, typically a murine antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting only the non-human complementarity determining regions (CDRs) into human framework and constant regions with or without retention of critical framework residues; and (c) transplanting the entire non-human variable domains, but "cloaking" them with a human-like section by replacement of surface residues. Such methods are disclosed in Morrison et al., *Proc. Natl. Acad. Sci.* 81: 6851–5 (1984); Morrison et al., *Adv. Immunol.* 44: 65–92 (1988); Verhoeyen et al., *Science* 239: 1534–1536 (1988); Padlan, *Molec. Immun.* 28: 489–498 (1991); and Padlan, *Molec. Immun.* 31: 169–217 (1994), all of which are hereby incorporated by reference in their entirety. Humanized anti-CD40L antibodies can be prepared as described in U.S. patent application Ser. No. 08/554,840 filed Nov. 7, 1995 also incorporated herein by reference in its entirety.

By "human antibody" is meant an antibody containing entirely human light and heavy chain as well as constant regions, produced by any of the known standard methods.

By "primatized antibody" is meant a recombinant antibody which has been engineered to contain the variable heavy and light domains of a monkey (or other primate) antibody, in particular, a cynomolgus monkey antibody, and which contains human constant domain sequences, preferably the human immunoglobulin gamma 1 or gamma 4 constant domain (or PE variant). The preparation of such antibodies is described in Newman et al., *Biotechnology,* 10: 1458–1460 (1992); also in commonly assigned Ser. Nos. 08/379,072, 08/487,550, or 08/746,361, all of which are incorporated by reference in their entirety herein. These antibodies have been reported to exhibit a high degree of homology to human antibodies, i.e., 85–98%, display human effector functions, have reduced immunogenicity, and may exhibit high affinity to human antigens.

By "antibody fragment" is meant an fragment of an antibody such as Fab, F(ab')₂, Fab' and scFv.

By "chimeric antibody" is meant an antibody containing sequences derived from two different antibodies, which typically are of different species. Most typically, chimeric antibodies comprise human and murine antibody fragments, and generally human constant and murine variable regions.

"B Cell Depleting Antibody" therein is an antibody or fragment that upon administration, results in demonstrable B cell depletion. Typically, such antibody will bind to a B cell antigen or B cell marker expressed on the surface of a B cell. Preferably, such antibody, after administration, typically within about several days or less, will result in a depletion of B cell number by about 50% or more. In a preferred embodiment, the B cell depleting antibody will be RITUXAN® (a chimeric anti-CD20 antibody) or one having substantially the same or at least 20–50% the cell depleting activity of RITUXAN®, over the same time period, preferably at least 90% thereof.

A "B cell surface marker" or "B cell target" or "B cell antigen" is an antigen expressed on the surface of a B cell which can be targeted with an antagonist which binds thereto. Exemplary B cell surface markers include the CD10, CD19, CD20, CD21, CD22, CD23, CD24, CD37, CD53, CD72, CD73, CD74, CDw75, CDw76, CD77, CDw78, CD79a, CD79b, CD80, CD81, CD82, CD83, CDw84, CD85 and CD86 leukocyte surface markers. A preferred B cell surface marker is preferentially expressed on B cells compared to other non-B cell tissues of a mammal and may be expressed on both precursor B cells and mature B cells.

The "CD20" antigen is a ~35 kDa, non-glycosylated phosphoprotein found on the surface of greater than 90% of B cells from peripheral blood or lymphoid organs. CD20 is expressed during early pre-B cell development and remains until plasma cell differentiation. CD20 is present on both normal B cells as well as malignant B cells. Other names for CD20 in the literature include "B-lymphocyte-restricted antigen" and "Bp35". The CD20 antigen is described in Clark et al. *PNAS (USA)* 82:1766(1985).

The "CD22" antigen refers to an antigen expressed on B cells, also known as "BL-CAM" and "LybB" that is involved in B cell signaling and an adhesion. (See Nitschke et al., *Curr. Biol.* 7:133 (1997); Stamenkovic et al., *Nature* 345:74 (1990)). This antigen is a membrane immunoglobulin-associated antigen that is tyrosine phosphorylated when membrane Ig is ligated. (Engel et al., *J. Etyp. Med.* 181(4):1521 1586 (1995)). The gene encoding this antigen has been cloned, and its lg domains characterized.

A B cell "antagonist" is a molecule which, upon binding to a B cell surface marker, destroys or depletes B cells in a mammal and/or interferes with one or more B cell functions, e.g. by reducing or preventing a humoral response elicited by the B cell. The antagonist preferably is able to deplete B cells (i.e. reduce circulating B cell levels) in a mammal treated therewith. Such depletion may be achieved via various mechanisms such antibody-dependent cell-mediated cytotoxicity (ADCC) and/or complement dependent cytotoxicity (CDC), inhibition of B cell proliferation and/or induction of B cell death (e.g. via apoptosis). Antagonists included within the scope of the present invention include antibodies, synthetic or native sequence peptides and small molecule antagonists which bind to the B cell marker, optionally conjugated with or fused to a cytotoxic agent.

"B cell depleting antibody" is an antibody that, upon in vivo administration, reduces the number of circulating B cells. Preferably, depletion will occur within about 24 hours of administration to levels which are at least 50% depletion or more. Most preferably, a cold anti-CD20 antibody will deplete B cells substantially as efficiently (within about 80–90% of the level of B cell depletion within same time) as Rituxan®.

"Antibody-dependent cell-mediated cytotoxicity" and "ADCC" refer to a cell mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, *Annu. Rev. Immunol* 9:457–92 (1991). To assess ADCC activity of a molecule of interest, an in vitro ADCC assay, such as that described in U.S. Pat. No. 5,500,362 or 5,821,337 maybe performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652–656 (1998).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRII subclasses, including allelic variants and alternatively spliced forms of these receptors. FcγRII receptors include FcγRIIA (an "activating receptor") and FcγRUB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daeon, *Annu. Rev. Immunol.* 15:203–234 (1997)). FcRs are reviewed in Ravetch and Kinet, *Annu. Rev. Immunol.* 9:457–92 (1991); Capel et al., *Immunomethods* 4:25–34 (1994); and de Haas et al., *J. Lab. Clin. Med.* 126:330–41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

"Complement dependent cytotoxicity" or "CDC" refers to the ability of a molecule to lyse a target in the presence of complement. The complement activation pathway is initiated by the binding of the first component of the complement system (Clq) to a molecule (e.g. an antibody) complexed with a cognate antigen. To assess complement activation, a CDC assay, e.g. as described in Gazzano-Santoro et al., *J. Immunol. Methods* 202:163 (1996), may be performed.

"Growth inhibitory" antagonists are those which prevent or reduce proliferation of a cell expressing an antigen to which the antagonist binds. For example, the antagonist may prevent or reduce proliferation of B cells in vitro and/or in vivo.

Antagonists which "induce apoptosis" are those which induce programmed cell death, e.g. of a B cell, as determined by binding of annexin V, fragmentation of DNA, cell shrinkage, dilation of endoplasmic reticulum, cell fragmentation, and/or formation of membrane vesicles (called apoptotic bodies).

The term "hypervariable region" when used herein refers to the amino acid residues of an antibody which are responsible for antigen-binding. The hypervariable region comprises amino acid residues from a "complementarity determining region" or "CDR" (e.g. residues 24–34 (L1), 50–56 (L2) and 89–97 (L3) in the light chain variable domain and 31–35 (H1), 50–65 (H2) and 95–102 (H3) in the heavy chain variable domain; Kabat et al., *Sequences of Proteins of*

*Immunological Interest,* 5th Ed. Public Health Service, National Institutes of Health, Bethesda, Md. (1991)) and/or those residues from a "hypervariable loop" (e.g. residues 26–32 (L1), 50–52 (L2) and 91–96 (L3) in the light chain variable domain and 26–32 (H1), 53–55 (H2) and 96–101 (H3) in the heavy chain variable domain; Chothia and Lesk.1. *Mol. Biol.* 196:901–917 (1987)). "Framework" or "FR" residues are those variable domain residues other than the hypervariable region residues as herein defined.

An antagonist "which binds" an antigen of interest, e.g. a B cell surface marker, is one capable of binding that antigen with sufficient affinity such that the antagonist is useful as a therapeutic agent for targeting a cell, i.e. a B cell, expressing the antigen.

An "anti-CD20 antibody" herein is an antibody that specifically binds CD20 antigen, preferably human CD20, having measurable B cell depleting activity, preferably having at least about 10%, more preferably at least 50%, and still more preferably at least 90%, the B cell depleting activity of RITUXAN® (see U.S. Pat. No. 5,736,137, incorporated by reference herein in its entirety).

An "anti-CD22 antibody" herein is an antibody that specifically binds CD22 antigen, preferably human CD22, having measurable B cell depleting activity, preferably having at least about 10% the B cell depleting activity of RITUXAN® (see U.S. Pat. No. 5,736,137, incorporated by reference herein in its entirety).

Specific examples of antibodies which bind the CD20 antigen include: "Rituximab" ("RITUXAN®") (U.S. Pat. No. 5,736,137, expressly incorporated herein by reference); yttrium-[90]-labeled 2B8 murine antibody "Y2B8" (U.S. Pat. No. 5,736,137, expressly incorporated herein by reference); murine IgG2a "B1" optionally labeled with $^{131}$I labeled B1 antibody (BEXXAR™) (U.S. Pat. No. 5,595,721, expressly incorporated herein by reference); murine monoclonal antibody "1F5" (Press et al. Blood 69(2): 584–591 (1987); and "chimeric 2H7" antibody (U.S. Pat. No. 5,677,180, expressly incorporated herein by reference).

Specific examples of antibodies which bind CD22 include Lymphocide™ reported by Immunomedics, now in clinical trials for non-Hodgkin's lymphoma.

The terms "rituximab" or "RITUXAN®" herein refer to the genetically engineered chimeric murine/human monoclonal antibody directed against the CD20 antigen and designated "C2B8" in U.S. Pat. No. 5,736,B7, expressly incorporated herein by reference. The antibody is an IgGI kappa immunoglobulin containing murine light and heavy chain variable region sequences and human constant region sequences. Rituximab has a binding affinity for the CD20 antigen of approximately 8.0 nM.

An "isolated" antagonist is one which has been identified and separated and/or recovered from a component of its natural environment. Contaminant components of its natural environment are materials which would interfere with diagnostic or therapeutic uses for the antagonist, and may include enzymes, hormones, and other proteinaceous or nonproteinaceous solutes. In preferred embodiments, the antagonist will be purified (1) to greater than 95% by eight of antagonist as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antagonist includes the antagonist in situ within recombinant cells since at least one component of the antagonist's natural environment will not be present. Ordinarily, however, isolated antagonist will be prepared by at least one purification step.

"Mammal" for purposes of treatment refers to any animal classified as a mammal, including humans, domestic and farm animals, and zoo, sports, or pet animals, such as dogs, horses, cats, cows, etc. Preferably, the mammal is human.

"Treatment" refers to both therapeutic treatment and prophylactic or preventative measures. Those in need of treatment include those already with the disease or disorder as well as those in which the disease or disorder is to be prevented. Hence, the mammal may have been diagnosed as having the disease or disorder or may be predisposed or susceptible to the disease.

B Cell Malignancy

According to the present invention this includes any B cell malignancy, e.g., B cell lymphomas and leukemias. Preferred examples include Hodgkin's disease (all forms, e.g., relapsed Hodgkin's disease, resistant Hodgkin's disease) non-Hodgkin's lymphomas (low grade, intermediate grade, high grade, and other types). Examples include small lymphocytic/B cell chronic lymphocytic leukemia (SLL/B-CLL), lymhoplasmacytoid lymphoma (LPL), mantle cell lymphoma (MCL), follicular lymphoma (FL), diffuse large cell lymphoma (DLCL), Burkitt's lymphoma (BL), AIDS-related lymphomas, monocytic B cell lymphoma, angioimmunoblastic lymphoadenopathy, small lymphocytic, follicular, diffuse large cell, diffuse small cleaved cell, large cell immunoblastic lymphoblastoma, small, non-cleaved, Burkitt's and non-Burkitt's, follicular, predominantly large cell; follicular, predominantly small cleaved cell; and follicular, mixed small cleaved and large cell lymphomas. See, Gaidono et al., "Lymphomas", IN CANCER: PRINCIPLES & PRACTICE OF ONCOLOGY, Vol. 2: 2131–2145 (DeVita et al., eds., 5$^{th}$ ed. 1997).

Other types of lymphoma classifications include immunocytomal Waldenstrom's MALT-type/monocytoid B cell, mantle cell lymphoma B-CLL/SLL, diffuse large B-cell lymphoma, follicular lymphoma, and precursor B-LBL.

As noted, B cell malignancies further include especially leukemias such as ALL-L3 (Burkitt's type leukemia), chronic lymphocytic leukemia (CLL), chronic leukocytic leukemia, acute myelogenous leukemia, acute lymphoblastic leukemia, chronic lymphocytic leukemia, chronic myelogenous leukemia, lymphoblastic leukemia, lymphocytic leukemia, monocytic leukemia, myelogenous leukemia, and promyelocytic leukemia and monocytic cell leukemias.

"Autoimmune disease" herein includes any autoimmune disease wherein elimination or depletion or inhibition of the activity or proliferation of B cells is therapeutically beneficial. Such autoimmune diseases will include in particular T and B cell mediated autoimmune diseases. Examples thereof include: the treatment or prevention of autoimmune, inflammatory, proliferative and hyperproliferative diseases, and of cutaneous manifestations of immunologically medicated diseases (e.g., rheumatoid arthritis, lupus erythematosus, systemic lupus erythematosus, Hashimotos thyroiditis, multiple sclerosis, myasthenia gravis, type 1 diabetes, uveitis, nephrotic syndrome, psoriasis, atopical dermatitis, contact dermatitis and further eczematous dermatitides, seborrheic dermatitis, Lichen planus, Pemplugus, bullous pemphigus, Epidermolysis bullosa, urticaria, angioedemas, vasculitides, erythema, cutaneous eosinophilias, Alopecia areata, etc.); the treatment of reversible obstructive airways disease, intestinal inflammations and allergies (e.g., inflammatory bile disease, Coeliac disease, proctitis, eosinophilia gastroenteritis, mastocytosis, Crohn's disease and ulcerative colitis), food-related allergies (e.g., migraine, rhinitis and eczema), and other types of allergies.

Also, the subject combination therapy is useful for treating malignancies, particularly solid tumors or late stage malignancies wherein B cells promote tumor growth, maintenance and/or metastasis but wherein B cells are not themselves the origin of the malignancy (not B cell malignancy such as non-Hodgkin's lymphoma).

Cell therapy includes any therapy wherein a potentially immunogenic cell is introduced into a subject, e.g. isogeneic, allogeneic or xenogeneic, which potentially may contain a tetrologus gene, e.g. one encoding a therapeutic polypeptide.

Gene therapy includes any therapy wherein a DNA or RNA sequence is introduced that modulates (inhibits or enhances) or provides for the expression of a gene normally or not normallyl expressed, e.g. one involved in a disease. Typically, the DNA or RNA will be comprised in a vector, e.g. plasmid, virus or in the genome of a cell, e.g. mammalian cell. Alternatively, the DNA or RNA may be "naked" or comprised in a stabilizing or targeting material, e.g. liposome. Examples include adenoviral, poxviruses, and other viral vectors, liposomal DNA formulations, etc.

The expression "therapeutically effective amount" refers to an amount of the naked antibody or radiolabeled antibody which is effective for preventing, ameliorating or treating the disease in question, e.g. B cell malignancy.

The term "immunosuppressive agent" as used herein for adjunct therapy refers to substances that act to suppress or mask the immune system of the mammal being treated herein. This would include substances that suppress cytokine production, downregulate or suppress self-antigen expression, or mask the MHC antigens. Examples of such agents include 2-amino-6-aryl-5-substituted pyrimidines (see U.S. Pat. No. 4,665,077, the disclosure of which is incorporated herein by reference), azathioprine; cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporin A; steroids such as glucocorticosteroids, e.g., prednisone, methylprednisolone, and dexamethasone; cytokine or cytokine receptor antagonists including anti-interferon-α, β- or δ-antibodies, anti-tumor necrosis factor-α antibodies, anti-tumor necrosis factor-β antibodies, anti-interleukin-2 antibodies and anti-IL-2 receptor antibodies; anti-LFA-1 antibodies, including anti-CD1 1a and anti-CD18 antibodies; anti-L3 T4 antibodies; heterologous anti-lymphocyte globulin; pan-T antibodies, preferably anti-CD3 or anti-CD4/CD4a antibodies; soluble peptide containing a LFA-3 binding domain (WO 90/08187 published 7/26/90), streptolanase; TGF-β; streptodornase; RNA or DNA from the host; FK506; RS-61443; deoxyspergualin; rapamycin; T-cell receptor (Cohen et al., U.S. Pat. No. 5,114,721); T-cell receptor fragments (Offner et al., Science, 251: 430–432 (1991); WO 90/11294; Laneway, Nature, 341: 482 (1989); and WO 91/01133); and T cell receptor antibodies (EP 340,109) such as T10B9.

The term "cytotoxic agent" as used herein refers to a substance that inhibits or 20 prevents the function of cells and/or causes destruction of cells. The term is intended to include radioactive isotopes (e.g. $^{123}$I, $^{125}$I, $^{131}$I, $^{111}$In, $^{131}$In, $^{52}$P, $^{64}$C, $^{67}$Cu, $^{211}$At, $^{177}$Lu, $^{90}$Y, $^{186}$Re, $^{212}$Pb, $^{212}$Bi, $^{47}$Sc, $^{105}$Rh, $^{104}$Pd, $^{153}$Sm, $^{188}$Re, $^{199}$Au, $^{211}$At and $^{213}$Bi), chemotherapeutic agents, and toxins such as small molecule toxins or enzymatically active toxins of bacterial, fungal, plant or animal origin, or fragments thereof.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime nitrogen mustards such as chiorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (Taxotere, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and antiandrogens such as flutamide, nilutamide, bicalutamide, leuprolide, and goserelin; and pharmaceutically acceptable salts, acids or derivatives of any of the above.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-$\alpha$ and -$\beta$; mullerian-inhibiting substance; mouse gonadotropin-associated peptide; inhibin; activin; vascular endothelial growth factor; integrin; thrombopoietin (TPO); nerve growth factors such as NGF-13; platelet-growth factor; transforming growth factors (TGFs) such as TGF-$\alpha$ and TGF-$\beta$; insulin-like growth factor-I and -II; erythropoietin (EPO); osteoinductive factors; interferons such as interferon-$\alpha$, -$\beta$, and -$\gamma$; colony stimulating factors (CSFs) such as macrophage-CSF (M-CSF); granulocytemacrophage-CSF (GM-CSF); and granulocyte-CSF (G-CSF); interleukins (ILs) such as IL-1, IL-1a, IL-2, IL-g, IL-4, IL-5, IL-6, IL-7, IL-8, IL-9, IL-11, IL-12, IL-15; a tumor necrosis factor such as TNF-$\alpha$ or TNF-$\beta$; and other polypeptide factors including LIF and kit ligand (KL). As used herein, the term cytokine includes proteins from natural sources or from recombinant cell culture and biologically active equivalents of the native sequence cytokines.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions,* 14, pp. 375–382, 615th Meeting Belfast (1986) and Stella et al., "Prodrugs: A Chemical Approach to Targeted Drug Delivery," *Directed Drug Delivery,* Borchardt et al, (ed.), pp. 247–267,Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, 13-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

A "liposome" is a small vesicle composed of various types of lipids, phospholipids and/or surfactant which is useful for delivery of a drug (such as the antagonists disclosed herein and, optionally, a chemotherapeutic agent) to a mammal. The components of the liposome are commonly arranged in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.
Production of Antibodies The subject invention uses antibodies to CD20 and CD22. These antibodies will be provided by known methods. As noted, antibodies to both these antigens are well known.

Exemplary techniques for the production of the antibodies used in accordance with the present invention are described.

(i) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g. 100 $\mu$g or 5 $\mu$g of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal Antibodies

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., *Nature,* 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice,* pp. 59–103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Manassas, Va., USA. Human myeloma and mouse-human heteromyeloma cell lines also have been described for the production of human monoclonal antibodies (Kozbor, J. *Immunol.*, 133:3001 (1984); Brodeur et al., *Monoclonal Antibody Production Techniques and Applications*, pp. 51–63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the 30 Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59–103 (Academic Press, 1986)). Suitable culture media for this purpose include, for example, D-MEM or RPML-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., *Curr. Opinion in Immunol.*, 5:256–262 (1993) and Pluckthun, *Immunol. Revs.*, 130:151–188 (1992).

Another method of generating specific antibodies, or antibody fragments, reactive against a CD20 or CD22 is to screen expression libraries encoding immunoglobulin genes, or portions thereof, expressed in bacteria with a CD20 or CD22 protein or peptide. For example, complete Fab fragments, $V_H$ regions and Fv regions can be expressed in bacteria using phage expression libraries. See for example, Ward et al., *Nature* 341: 544–546 (1989); Huse et al., *Science* 246: 1275–1281 (1989); and McCafferty et al., *Nature* 348: 552–554 (1990). Screening such libraries with, for example, a CD22 or CD20 peptide, can identify immunoglobulin fragments reactive with CD22 or CD20. Alternatively, the SCID-hu mouse (available from Genpharm) can be used to produce antibodies or fragments thereof.

In a further embodiment, antibodies or antibody fragments can be isolated from antibody phage libraries generated using the techniques described in McCafferty et al., *Nature*, 348:552–554(1990). Clackson et al., *Nature*, 352:624–628 (1991) and Marks et al., *J. Mol. Biol.*, 222:581–597 (1991) describe the isolation of murine and human antibodies, respectively, using phage libraries. Subsequent publications describe the production of high affinity (nM range) human antibodies by chain shuffling (Marks et al., *Bio/Technology*, 10:779–783 (1992)), as well as combinatorial infection and in vivo recombination as a strategy for constructing very large phage libraries (Waterhouse et al., *Nuc. Acids. Res.*, 21:2265–2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Natl Acad. ScL USA*, 81:6851 (1984)), or by covalently joining to the immunoglobulin coding sequence all or part of the coding sequence for a non-immunoglobulin polypeptide.

Typically, such non-immunoglobulin polypeptides are substituted for the constant domains of an antibody, or they are substituted for the variable domains of one antigencombining site of an antibody to create a chimeric bivalent antibody comprising one antigen-combining site having specificity for an antigen and another antigen-combining site having specificity for a different antigen.

(iii) Humanized Antibodies

Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522–525 (1986); Reichmann et al., *Nature*, 332:323–327 (1988); Verhoeyen et al., *Science*, 239:1534–1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so called "best-fit" method, the sequence of the variable domain of a rodent antibody is screened against the entire library of known human variable-domain sequences. The human sequence which is closest to that of the rodent is then accepted as the human framework region (FR) for the humanized antibody (Suns et al., *J. Immunol.*, 151:2296 (1993); Chothia et al., *J. Mol. Biol*, 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i. e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

(iv) Primatized Antibodies

Another highly efficient means for generating recombinant antibodies is disclosed by Newman, *Biotechnology*, 10: 1455–1460 (1992). More particularly, this technique results in the generation of primatized antibodies which contain monkey variable domains and human constant sequences. This reference is incorporated by reference in its entirety herein. Moreover, this technique is also described in commonly assigned U.S. application Ser. No. 08/379,072, filed on Jan. 25, 1995, which is a continuation of U.S. Ser. No. 07/912,292, filed Jul. 10, 1992, which is a continuation-in-part of U.S. Ser. No. 07/856,281, filed Mar. 23, 1992, which is finally a continuation-in-part of U.S. Ser. No. 07/735,064, filed Jul. 25, 1991. Ser. No. 08/379,072 and the parent application thereof all of which are incorporated by reference in their entirety herein.

This technique modifies antibodies such that they are not antigenically rejected upon administration in humans. This technique relies on immunization of cynomolgus monkeys with human antigens or receptors. This technique was developed to create high affinity monoclonal antibodies directed to human cell surface antigens.

Identification of macaque antibodies to human CD20 or CD22 by screening of phage display libraries or monkey heterohybridomas obtained using B lymphocytes from CD20 or CD22 immunized monkeys can be performed using the methods described in commonly assigned U.S. application Ser. No. 08/487,550, filed Jun. 7, 1995, incorporated by reference in its entirety herein.

Antibodies generated using the methods described in these applications have previously been reported to display human effector function, have reduced immunogenicity, and long serum half-life. The technology relies on the fact that despite the fact that cynomolgus monkeys are phylogenetically similar to humans, they still recognize many human proteins as foreign and therefore mount an immune response. Moreover, because the cynomolgus monkeys are phylogenetically close to humans, the antibodies generated in these monkeys have been discovered to have a high degree of amino acid homology to those produced in humans. Indeed, after sequencing macaque immunoglobulin light and heavy chain variable region genes, it was found that the sequence of each gene family was 85–98% homologous to its human counterpart (Newman et al., 1992). The first antibody generated in this way, an anti-CD4 antibody, was 91–92% homologous to the consensus sequence of human immunoglobulin framework regions (Newman et al., 1992).

(v) Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region PH) gene in chimeric and germ-line mutant mice results in complete inhibition of endogenous antibody production. Transfer of the human germ-line immunoglobulin gene array in such germ line mutant mice will result in the production of human antibodies upon antigen challenge. See, e.g., Jakobovits et al., *Proc. Mad. Acad. Sci. USA*, 90:2551 (1993); Jakobovits et al., *Nature*, 362:255–258 (1993); Bruggermann et al., *Year in immuno.*, 7:33 (1993); and U.S. Pat. Nos. 5,591,669, 5,589,369 and 5,545,807.

Alternatively, phage display technology (McCafferty et al., *Nature* 348:552–553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S. and Chiswell, David J., *Current Opinion in Structural Biology* 3:564–571 (1993). Several sources of V-gene segments can be used for phage display. Clackson et al., *Nature*, 352:624–628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self antigens) can be isolated essentially following the techniques described by Marks et al, *J. Mol. Biol*, 222:581–597 (1991), or Griffith et al., *EMBO J.* 12:725–734 (1993). See, also, U.S. Pat. Nos. 5,565,332 and 5,573,905.

Human antibodies may also be generated by in vitro activated B cells (see U.S. Pat. Nos. 20 5,567,610 and 5,229,275). A preferred means of generating human antibodies using SCID mice is disclosed in commonly-owned, co-pending applications.

(vi) Antibody Fragments

Various techniques have been developed for the production of antibody fragments. Traditionally, these fragments were derived via proteolytic digestion of intact antibodies (see, e.g., Morimoto et al, *Journal of Biochemical and Biophysical Methods* 24:107–117 (1992) and Brennan et al., *Science*, 229:81 (1985)). However, these fragments can now be produced directly by recombinant host cells. For example, the antibody fragments can be isolated from the antibody phage libraries discussed above. Alternatively, Fab'-SH fragments can be directly recovered from E. coli and chemically coupled to form F(ab')2 fragments (Carter et al., Bio/Technology 10: 163–167 (1992)). According to another approach, F(ab')2 fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. The antibody fragment may also be a "linear antibody", e.g., as described in U.S. Pat. No. 5,641,870 for example. Such linear antibody fragments may be monospecific or bispecific.

(vii) Bispecific Antibodies

Bispecific antibodies are antibodies that have binding specificities for at least two different epitopes. Exemplary bispecific antibodies may bind to two different epitopes of the B cell surface marker. Other such antibodies may bind a first B cell marker and further bind a second B cell surface marker. Alternatively, an anti-B cell marker binding arm may be combined with an arm which binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD 16) so as to focus cellular defense mechanisms to the B cell. Bispecific antibodies may also be used to localize cytotoxic agents to the B cell. These antibodies possess a B cell marker-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. F(ab)2 bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., *Nature,* 305:537–539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.,* 10:3655–3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CHI) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology,* 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side chains from the interface of the first antibody molecule are replaced with larger side chains (e.g. tyrosine or tryptophan). Compensatory "cavities" of identical or similar size to the large side chains are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science,* 229:81(1985) describe a procedure wherein intact antibodies are proteolytically cleaved to generate F(ab')2 fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from E. coli, which can be chemically coupled to form bispecific antibodies. Shalaby et al., *J. Exp. Med.,* 175:217–225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al.,*J. Immunol* 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60(1991).

Antibody Conjugates and Other Modifications

The subject therapies may first include the administration of antibody other than the radiolabeled CD22 antibody wherein the antibody is attached, e.g. to a cytotoxin or therapeutic moiety conjugate.

Chemotherapeutic agents useful in the generation of such antibody-cytotoxic agent conjugates have been described above.

Conjugates of an antibody and one or more small molecule toxins, such as a calicheamicin, a maytansine (U.S. Pat. No. 5,208,020), a trichothene, and CC 1065 are also contemplated herein. In one preferred embodiment of the invention, the antagonist is conjugated to one or more maytansine molecules (e.g. about 1 to about maytansine molecules per antagonist molecule). Maytansine may, for example, be converted to May SS-Me which may be reduced to May-SH3 and reacted with modified antagonist (Charm et al. *Cancer Research* 52:127–131(1992)) to generate a maytansinoid-antagonist conjugate.

Alternatively, the antibody may be conjugated to one or more calicheamicin molecules. The calicheamicin family of antibiotics are capable of producing double stranded DNA breaks at sub-picomolar concentrations. Structural analogues of calicheamicin which may be used include, but are not limited to, $\gamma_1^I$, $\alpha_2^I$, $\alpha_3^I$, N-acetyl-$\gamma_1^I$, PSAG and $O_1^I$, (Hinman et al. *Cancer Research* 53:3336–3342 (1993) and Lode et al, Cancer Research 58: 2925–2928 (1998)).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates antibody conjugated with a compound with nucleolytic activity (e.g. a ribonuclease or a DNA endonuclease such as a deoxyribonuclease; DNase).

As discussed above, a variety of radioactive isotopes are available for the production of radioconjugated antagonists. Examples include $At^{211}$, $I^{131}$, $I^{125}$, $Y^{90}$, $Re^{186}$, $RE^{188}$, $Sm^{153}$, $Bi^{212}$, $P^{32}$ and radioactive isotopes of Lu.

Conjugates of the antibody and cytotoxic agent may be made using a variety of bifunctional protein coupling agents such as N-succinimidyl-3-(2-pyriyldithiol) propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. *Science* 238: 1098 (1987). Carbon-14-labeled 1 isothiocyanatobenzyl-3-methyldiethylene triaminepentaacetic.acid (MX-DTPA) is an exemplary chelating agent for conjugation of radionucleotide to the antagonist. See WO94/11026. The linker may be a "cleavable linker" facilitating release of the cytotoxic drug in the cell. For example, an acid-labile linker, peptidase-sensitive linker, dimethyl linker or disulfide-containing linker (Charm et al. *Cancer Research* 52:127–131 (1992)) maybe used.

Alternatively, a fusion protein comprising the antibody and cytotoxic agent may be made, e.g. by recombinant techniques or peptide synthesis.

In yet another embodiment, the antibody may be conjugated to a "receptor" (such streptavidin) for utilization in tumor pretargeting wherein the antagonist-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

The antibodies of the present invention may also be conjugated with a prodrug activating enzyme which converts a prodrug (e.g. a peptidyl chemotherapeutic agent, see WO81/01145) to an active anti-cancer drug. See, for example, WO 88/07378 and U.S. Pat. No. 4,975,278.

The enzyme component of such conjugates includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic5-fluorocytosine into the anti-cancer drug, fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydratecleaving enzymes such as 13-galactosidase and neuraminidase useful for converting glycosylated prodrugs into free drugs; 13-lactamase useful for converting drugs derivatized with 13-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328:457–458 (1987)). Antagonist-abzyme conjugates can be prepared as described herein for delivery of the abzyme to a tumor cell population.

The enzymes of this invention can be covalently bound to the antagonist by techniques well known in the art such as the use of the heterobifunctional crosslinking reagents discussed above. Alternatively, fusion proteins comprising at least the antigen binding region of an antagonist of the invention linked to at least a functionally active portion of an enzyme of the invention can be constructed using recombinant DNA techniques well known in the art (see, e.g., Neuberger et al., Nature, 312:604–608 (1984)).

Other modifications of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol.

The antibodies disclosed herein may also be formulated as liposomes. Liposomes containing the antagonist are prepared by methods known in the art, such as described in Epstein et al., Proc. Natl. Acad. Sci. USA, 82:3688 (1985); Hwang et al., Proc. Natl Acad. Sci. USA, 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG derivatized phosphatidylethanolamine (PEG-PE). Liposomes are extruded through filters of defined pore size to yield liposomes with the desired diameter. Fab' fragments of an antibody of the present invention can be conjugated to the liposomes as described in Martin et al. J. Biol. Chem. 257:286–288 (1982) via a disulfide interchange reaction. A chemotherapeutic agent is optionally contained within the liposome. See Gabizon et al. J. National Cancer Inst. 81(19)1484 (1989).

Amino acid sequence modification(s) of protein or peptide antagonists described herein are contemplated. For example, it may be desirable to improve the binding affinity and/or other biological properties of the antibody. Amino acid sequence variants of the antibody are prepared by introducing appropriate nucleotide changes into the antibody encoding nucleic acid, or by peptide synthesis. Such modifications include, for example, deletions from, and/or insertions into and/or substitutions of, residues within the amino acid sequences of the antagonist. Any combination of deletion, insertion, and substitution is made to arrive at the final construct, provided that the final construct possesses the desired characteristics. The amino acid changes also may alter post-translational processes of the antagonist, such as changing the number or position of glycosylation sites.

A useful method for identification of certain residues or regions of the antibody that are preferred locations for mutagenesis is called "alanine scanning mutagenesis" as described by Cunningham and Wells Science, 244:1081–1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antagonist variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antagonist with an N-terminal methionyl residue or the antagonist fused to a cytotoxic polypeptide. Other insertional variants of the antagonist molecule include the fusion to the N- or C-terminus of the antagonist of an enzyme, or a polypeptide which increases the serum half-life of the antagonist.

Another type of variant is an amino acid substitution variant. These variants have at least one amino acid residue in the antagonist molecule replaced by different residue. The sites of greatest interest for substitutional mutagenesis of antibody antagonists include the hypervariable regions, but FR alterations are also contemplated. Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
| --- | --- | --- |
| Ala (A) | val; leu; ile | val |
| Arg (R) | lys; gin; asn | lys |
| Asn (N) | gln; his; asp, lys; arg | gln |
| Asp (D) | glu; asn | glu |
| Cys (C) | ser; ala | ser |
| Gln (Q | asn; glu | asn |
| Glu (E) | asp; gin | asp |
| Gly (G) | ala | ala |
| His (H) | asn; gin; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;

(2) neutral hydrophiuic: cys, ser, thr;

(3) acidic: asp, glu;

(4) basic: asn, gin, his, lys, arg;

(5) residues that influence chain orientation: gly, pro; and (6) aromatic: trp, tyr, phe.

Non-conservative substitutions will entail exchanging a member of one of these classes for another class.

Any cysteine residue not involved in maintaining the proper conformation of the antagonist also may be substituted, generally with serine, to improve the oxidative stability of the molecule and prevent aberrant crosslinking.

Conversely, cysteine bonds) may be added to the antagonist to improve its stability (particularly where the antagonist is an antibody fragment such as an Fv fragment).

A particularly preferred type of substitutional variant involves substituting one or more hypervariable region residues of a parent antibody (e.g. a humanized or human antibody). Generally, the resulting variants selected for further development will have improved biological properties relative to the parent antibody from which they are generated. A convenient way for generating such substitutional variants is affinity maturation using phage display. Briefly, several hypervariable region sites (e.g. 6–7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identified hypervariable region residues contributing significantly to antigen binding. Alternatively, or in addition, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antagonist. By altering is meant deleting one or more carbohydrate moieties found in the antagonist, and/or adding one or more glycosylation sites that are not present in the antagonist.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly seine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more seine or threonine residues to the sequence of the original antagonist (for O-linked glycosylation sites).

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antagonist.

It may be desirable to modify the antibodies used in the invention to improve effector function, e.g. so as to enhance antigen-dependent cell-mediated cyotoxicity (ADCC) and/or complement dependent cytotoxicity (CDC) of the antagonist. This may be achieved by introducing one or more amino acid substitutions in an Fc region of an antibody antagonist. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191–1195 (1992) and Shopes, *B. J. Immunol.* 148:2918–2922 (1992). Homodimeric antibodies with enhanced anti-tumor activity may also be prepared using heterobifunctional cross-linkers as described in Wolff et al *Cancer Research* 53:2560–2565 (1993). Alternatively, an antibody can be engineered which has dual Fc regions and may thereby have enhanced complement lysis and ADCC capabilities. See Stevenson et al. *Anti-Cancer Drug Design* 3:219–230 (1989).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgGI, IgG2, IgG3, or IgG4) that is responsible for increasing the in vivo serum half-life of the IgG molecule.

Pharmaceutical Formulations

Therapeutic formulations comprising cold anti-CD20 and radiolabeled anti-CD22 antibodies used in accordance with the present invention are prepared for storage by mixing an antagonist having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The antibodies may be in the same formulation or may be administered in difficult formulations. Administration can be concurrent or sequential, and may be effective in either order.

Exemplary anti-CD20 antibody formulations are described in WO98/56418, expressly incorporated herein by reference. This publication describes a liquid multidose formulation comprising 40 mg/mL rituximab, 25 mM acetate, 150 mM trehalose, 0.9% benzyl alcohol, 0.02% polysorbate 20 at pH 5.0 that has a minimum shelf life of two years storage at 2–8° C. Another anti-CD20 formulation of interest comprises 10 mg/mL rituximab in 9.0 mg/mL sodium chloride, 7.35 mg/mL sodium citrate dihydrate, 0.7 mg/mL polysorbate 80, and Sterile Water for Injection, pH 6.5.

Lyophilized formulations adapted for subcutaneous administration are described in WO97/04801 Such lyophilized formulations may be reconstituted with a suitable diluent to a high protein concentration and the reconstituted formulation may be administered subcutaneously to the mammal to be treated herein.

The formulation herein may also contain more than one active compound as necessary for the particular indication being treated, preferably those with complementary activities that do not adversely affect each other. For example, it may be desirable to further provide a chemotherapeutic agent, cytokine or immunosuppressive agent (e.g. one which acts on T cells, such as cyclosporin or an antibody that binds T cells, e.g. one which binds LFA-1). The effective amount of such other agents depends on the amount of antagonist present in the formulation, the type of disease or disorder or treatment, and other factors discussed above. These are generally used in the same dosages and with administration routes as used hereinbefore or about from 1 to 99% of the heretofore employed dosages.

The active ingredients may also be entrapped in microcapsules prepared, for example, by 30 coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin micro spheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained release preparations include semipermeable matrices of solid hydrophobic polymers containing the antagonist, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, noir degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. The formulations to be used for in vivo administration must be sterile. This is readily accomplished by filtration through sterile filtration membranes.

Treatment with Cold Anti-CD20 and Hot (Radiolabeled) Anti-CD22 Antibody or Antibody Fragment A composition comprising cold CD20 antibody, e.g. Rituxan® as a radiolabeled anti-CD22 antibody, preferably $^{90}Y$ (radiolabeled by use of MXDTPA as the chelate) will be formulated, dosed, and administered in a fashion consistent with good medical practice. Factors for consideration in this context include the particular B cell malignancy, or other condition, e.g. autoimmune, allergy, inflammatory disorder, cell therapy or gene therapy, the particular mammal being treated, the clinical condition of the individual patient, the cause of the disease or disorder, the site of delivery of the agent, the method of administration, the scheduling of administration, and other factors known to medical practitioners. The therapeutically effective amount of the antagonist to be administered will be governed by such considerations.

The CD20 antibody and the radiolabeled CD22 antibody may be in the same or in different formulations. These formulations can be administered separately or concurrently, and in either order. Preferably, the cold CD20 antibody will be administered separately from the radiolabeled CD22.

As a general proposition, the therapeutically effective amount of an antibody administered parenterally per dose will typically be in the range of about 0.1 to 500 mg/kg of patient body weight per day, with the typical initial range of antagonist used being in the range of about 2 to 100 mg/kg.

The preferred anti-CD20 antibody is RITUXAN®. Suitable dosages for such antibody are, for example, in the range from about 20 mg/m2 to about 1000 mg/m2. The dosage of the antibody may be the same or different from that presently recommended for RITUXAN® for the treatment of non-Hodgkin's lymphoma. For example, one may administer to the patient one or more doses of substantially less than 375 mg/m2 of the antibody, e.g. where the dose is in the range from about 20 mg/m$^2$ to about 250 mg/m$^2$, for example from about 50 mg/m$^2$ to about 200 mg/m$^2$. The amount of the radiolabeled anti-CD22 antibody will depend upon factors such as the particular therapeutic radiolabel, e.g. whether it is an α, β or δ emitter. Methods for determining appropriate dosages of radiation are well known. Preferably, a dosage will be selected that does not result in myelosuppression severe enough to require one marrow or stem cell transplant.

Preferably, the anti-CD20 antibody will possess substantially B cell deleting activity and will induce apoptosis of B cells, comparable to Rituxan®.

Moreover, one may administer one or more initial doses of the CD20 or radiolabeled anti-CD22 antibody followed by one or more subsequent dose(s), wherein the mg/m$^2$ dose of the antibody in the subsequent doses) exceeds the mg/m$^2$ dose of the antibody in the initial dose(s). For example, the initial dose may be in the range from about 20 mg/m$^2$ to about 250 mg/m$^2$ (e.g. from about 50 mg/m$^2$ to about 200 mg/m$^2$) and the subsequent dose may be in the range from about 250 mg/m$^2$ to about 1000 mg/m$^2$.

As noted above, however, these suggested amounts of both CD20 and CD22 antibody are subject to a great deal of therapeutic discretion. The key factor in selecting an appropriate dose and scheduling is the result obtained, as indicated above. For example, relatively higher doses may be needed initially for the treatment of ongoing and acute diseases. To obtain the most efficacious results, depending on the particular B cell malignancy, the antagonist is administered as close to the first sign, diagnosis, appearance, or occurrence of the disease or disorder as possible or during remissions of the disease or disorder.

The antibodies are administered by any suitable means, including parenteral, subcutaneous, intraperitoneal, intrapulmonary, and intranasal, and, if desired for local immunosuppressive treatment, intralesional administration. Parenteral infusions include intramuscular, intravenous, intraarterial, intraperitoneal, or subcutaneous administration. In addition, the antibody may suitably be administered by pulse infusion, e.g., with declining doses of the antibody. Preferably the dosing is given by injections, most preferably intravenous or subcutaneous injections, depending in part on whether the administration is brief or chronic.

One additionally may administer other compounds, such as chemotherapeutic agents, immunosuppressive agents and/or cytokines with the antibodies herein. The combined administration includes co-administration, using separate formulations or a single pharmaceutical formulation, and consecutive administration in either order, wherein preferably there is a time period while both (or all) active agents simultaneously exert their biological activities.

Aside from administration of antibodies to the patient the present application contemplates administration of antibodies by gene therapy. Such administration of nucleic acid encoding the antibodies is encompassed by the expression "administering a therapeutically effective amount of an antagonist". See, for example, WO96/07321 published Mar. 14, 1996 concerning the use of gene therapy to generate intracellular antibodies.

There are two major approaches to getting the nucleic acid (optionally contained in a vector) into the patient's cells; in vivo and ex vivo. For in vivo delivery the nucleic acid is injected directly into the patient, usually at the site where the antagonist is required. For ex vivo treatment, the patient's cells are removed, the nucleic acid is introduced into these isolated cells and the modified cells are administered to the patient either directly or, for example, encapsulated within porous membranes which are implanted into the patient (see, e.g. U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAF-dextran, the calcium phosphate precipitation method, etc. A commonly used vector for ex vivo delivery of the gene is a retrovirus.

The currently preferred in vivo nucleic acid transfer techniques include transfection with viral vectors (such as adenovirus, Herpes simplex I virus, or adeno associated virus) and lipid-based systems (useful lipids for lipid-mediated transfer of the gene are DOTMA, DOPE and DC-Chol, for example). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., .l. Biol. Chem 262:4429–4432 (1987); and Wagner et al., Proc. Natl. Acad. Sci. USA 87:3410–3414(1990). For review of the currently known gene marking and gene therapy protocols see Anderson et al., Science 256:808–813 (1992). See also WO 93/25673 and the references cited therein.

Articles of Manufacture

In another embodiment of the invention, an article of manufacture containing materials useful for the treatment of the diseases or disorders described above is provided.

The article of manufacture comprises a container and a label or package insert on or associated with the container. Suitable containers include, for example, bottles, vials, syringes, etc. The containers may be formed from a variety of materials such as glass or plastic. The container holds or contains a composition which is effective for treating the disease or disorder of choice and may have a sterile access port (for example the container may be an intravenous solution bag or a vial having a stopper pierceable by a hypodermic injection needle). As whole, there may be one or several compositions. At least one active agent in one of those compositions is a cold CD20 antibody, preferably one having substantial B cell depleting activity and at least one antibody is therapeutically radiolabeled anti-CD22 antibody or fragment, preferably $^{90}$Y radiolabeled antibody. The label or package insert indicates that the composition is used for treating a patient having or predisposed to B cell malignancy, such as those listed hereinabove or other conditions or treatment wherein inhibition of B cells is desirable, e.g. autoimmune disease, transplant, gene therapy, cell therapy or inflammatory condition. The article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Further details of the invention are illustrated by the following non-limiting Examples. The disclosures of all citations in the specification are expressly incorporated herein by reference.

The antibodies of the invention may be administered to a human or other animal in accordance with the aforementioned methods of treatment in an amount sufficient to produce such effect to a therapeutic or prophylactic degree. Such antibodies of the invention can be administered to such human or other animal in a conventional dosage form prepared by combining the antibody of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables.

The routine of administration of the antibody (or fragment thereof) of the invention may be oral, parenteral, by inhalation or topical. The term parenteral as used herein includes intravenous, intraperitoneal, intramuscular, subcutaneous, rectal or vaginal administration. The subcutaneous and intramuscular forms of parenteral administration are generally preferred.

The daily parenteral and oral dosage regimes for employing compounds of the invention to prophylactically or therapeutically induce immunosuppression, or to therapeutically treat carcinogenic tumors will generally be in the range of about 0.05 to 100, but preferably about 0.5 to 10, milligrams per kilogram body weight per day.

The antibodies of the invention may also be administered by inhalation. By "inhalation" is meant intranasal and oral inhalation administration. Appropriate dosage forms for such administration, such as an aerosol formulation or a metered dose inhaler, may be prepared by conventional techniques. The preferred dosage amount of a compound of the invention to be employed is generally within the range of about 10 to 100 milligrams.

The antibodies of the invention may also be administered topically. By topical administration is meant non-systemic administration and includes the application of an antibody (or fragment thereof) compound of the invention externally to the epidermis, to the buccal cavity and instillation of such an antibody into the ear, eye and nose, and where it does not significantly enter the blood stream. By systemic administration is meant oral, intravenous, intraperitoneal and intramuscular administration. The amount of an antibody required for therapeutic or prophylactic effect will, of course, vary with the antibody chosen, the nature and severity of the condition being treated and the animal.

Combination Therapy of Invention

The present invention relates to the combined use of a cold anti-CD20 antibody and a radiolabeled anti-CD22 antibody targeted to extracellular determinants of CD20 and CD22. CD20 and CD22 are both antigens present on B-cells. These antibodies are selectively reactive under immunological conditions to those determinants of CD20 and CD22 displayed on the surface of B-cells and accessible to the antibody from the extracellular milieu.

The term "selectively reactive" or "specific to" includes reference to the preferential association of an antibody, in whole or part, with a cell or tissue bearing the CD22 or CD20 target molecule and not to cells or tissues lacking that target molecule. It is, of course, recognized that a certain degree of nonspecific interaction may occur between a molecule and a non-target cell or tissue. Nevertheless, specific binding, may be distinguished as mediated through specific recognition of the target CD22 or CD20 molecule. Typically specific binding results in a much stronger association between the delivered molecule and cells bearing CD22 or CD20 than between the bound molecule and cells lacking CD22 or CD20. Specific binding typically results in greater than two-fold, preferably greater than five-fold, more preferably greater than ten-fold and most preferably greater than one hundred-fold increase in amount of bound ligand (per unit time) to a cell or tissue bearing CD22 or CD20 as compared to a cell or tissue lacking CD22 or CD20. Specific binding to a protein under such conditions requires an antibody that is selected for its specificity for a particular protein. A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual,* Cold Spring Harbor Publications, New York, for a description of immunoassay formats and conditions that can be used to determine specific immunoreactivity.

Anti-CD20 Antibodies

The anti-CD20 antibody preferably will comprise a chimeric, humanized or human monoclonal antibody that specifically bind CD20 or a fragment thereof. Most preferably, the anti-CD20 antibody will comprise RITUXAN®, the nucleic acid sequence and amino acid sequence of which is reported in U.S. Pat. No. 5,736,137, incorporated by reference in its entirety herein. This chimeric anti-CD20 antibody very effectively depletes B-cells and has been approved for use by the FDA for treating non-Hodgkin's lymphoma. However, humanized and human monoclonal antibodies may also be used.

The radiolabeled anti-CD22 antibody will preferably comprise a chimeric, humanized or human monoclonal antibody or binding fragment thereof specific to CD22. In the preferred embodiment, a $^{90}$Y radiolabeled humanized monoclonal antibody, the sequence of which is disclosed in Leung et al in U.S. Pat. No. 5,789,554, issued Aug. 4, 1998, will be utilized. This reference is also incorporated by reference in its entirely herein. However, other monoclonal antibodies and binding fragments can be substituted therefor.

Additionally, the use of radionuclides other than $^{90}$Y is contemplated, e.g., 131I, $^{67}$CU, 32p, 125I, $^{186}$Re, $^{188}$Re, $^{211}$At and the like. Suitable radioisotopes include α, β, and γ-emitters, Auger electron emitters, and neutron capturing agents that emit α-particles or a radioisotope that decays by electron capture.

The radiolabel may be attached directly or indirectly to the antibody or fragment, e.g., by use of a chelating agent. Suitable chelators include by way of example DTPA and DETA.

Suitable antibody fragments include any antibody which lacks substantially all the Fc region of a native antibody. These include in particular scFv, dsFv, Fab, F(ab$^1$)$_2$, F(ab)$_2$, Fab, and the like.

As noted, the anti-CD20 antibody and radiolabeled anti-CD22 antibody can be administered separately or in combination, and in either order. Preferably, the anti-CD20 antibody is administered initially in therapeutically effective amounts, followed by the radiolabeled anti-CD22 antibody.

Binding Affinity of Antibodies

The antibodies used in this invention are capable of specifically binding an extracellular epitope of CD22 or CD20. An anti-CD22 or anti-CD20 antibody has binding affinity for CD22 or CD20 if the antibody binds or is capable of binding CD22 or CD20 as measured or determined by standard antibody-antigen assays, for example, competitive assays, saturation assays, or standard immunoassays such as ELISA or RIA. This definition of specificity applies to single heavy and/or light chains, CDRS, fusion proteins or fragments of heavy and/or light chains, that are specific for CD22 or CD20 if they bind CD22 alone or in combination.

In competition assays the ability of an antibody to bind a ligand is determined by detecting the ability of the antibody to compete with the binding of a compound known to bind the ligand. Numerous types of competitive assays are known and are discussed herein. Alternatively, assays that measure binding of a test compound in the absence of an inhibitor may also be used. For instance, the ability of a molecule or other compound to bind CD22 can be detected by labeling the molecule of interest directly or the molecule be unlabeled and detected indirectly using various sandwich assay formats. Numerous types of binding assays such as competitive binding assays are known (see, e.g., U.S. Pat. Nos. 3,376,110 and 4,016,043, and Harlow and Lane, *Antibodies: A Laboratory Manual,* Cold Spring Harbor Publications, N.Y. (1988), which are incorporated herein by reference). Assays for measuring binding of a test compound to one component alone rather than using a competition assay are also available. For instance, antibodies can be used to identify the presence of the ligand. Standard procedures for monoclonal antibody assays, such as ELISA, may be used (see, Harlow and Lane, supra). For a review of various signal producing systems which may be used see, U.S. Pat. No. 4,391,904, which is incorporated herein by reference.

The dosages of anti-CD20 to be used in the present invention may vary depending on the patient and the antibody used. Chimeric anti-CD20 antibody such as rituximab may be administered at a dosage of at least about 50 mg/m$^2$ weekly for at least 4 weeks. A particularly preferred dosage regimen is about 375 mg/m$^2$ weekly for four weeks.

As noted, preferably after administration of the anti-CD20 antibody, a radiolabeled anti-CD22 antibody will be administered, i.e., one which is attached to a therapeutic radiolabel. Preferred radiolabels are beta emitting isotopes such as $^{90}$Y or $^{131}$I, but any radioisotope may be used so long as it may be effectively conjugated to the antibody, it has a relatively short decay range, and it succeeds in killing nearby cells, i.e., the cells to which it is targeted. Typically, the radiolabel will be attached by use of a chelator, e.g., DTPA.

A patient preferably will be treated within one week after administration of the depleting anti-CD20 antibody, so long as they are not severely cytopenic, e.g., platelets <150,000. If the patient is cytopenic following treatment with the depleting antibody, recovery should be allowed to occur, e.g. nadir AGC >1000 or platelets >150,000, before radioimmunotherapy. In cases where cell recovery in the peripheral blood and/or bone marrow is permitted to occur, more depleting antibody may be administered directly before immunotherapy. Such a secondary dosage may be administered, for example, at about 250 mg/m² for about two weeks directly before or overlapping with radioimmunotherapy.

Dosages of radiolabeled antibodies will also vary depending on the patient, the antibody specificity, half-life, radioisotope stability, etc., and of course, the extent of disease. Radiolabeled anti-CD22 antibodies are typically administered at a dosage of about 0.001 to 150 mCi/kg, more preferably 0.1 to 50 mCi/kg, still more preferably 0.1 to 30 mCi/kg. Another suitable dosage will range from 10 to 30 mCi/kg. The dosages of radiation can be determined by the ordinary artisan.

It should be clear that the treatment methods disclosed herein may be combined with other known treatment methods such as chemotherapy or radiotherapy. Bone marrow or peripheral blood stem cells may be harvested from said patient subsequent to treatment with anti-CD20 antibody and prior to treatment with said radiolabeled antibody in order to effect autologous bone marrow or stem cell transplantation after radiotherapy.

It may also be useful to treat patients with cytokines in order to up-regulate the expression of CD20 or other target protein on the surface of cancerous B cells prior to administration of the depleting antibody or the radiolabeled antibody. For up-regulation of CD20, cytokines useful for this purpose are IL-4, GM-CSF and TNF-alpha. Cytokines may also be administered simultaneously with or prior to or subsequent to administration of the depleting antibody or radiolabeled antibody in order to stimulate immune effector functions. Cytokines useful for this purpose include interferon alpha, GM-CSF and G-CSF.

Chemotherapeutic regimens may be used to supplement the therapies disclosed herein, and may be administered simultaneously with or sequentially in any order with administration of said radiolabeled antibody. The chemotherapy regimen may be selected from the group consisting of CHOP, ICE, Mitozantrone, Cytarabine, DVP, ATRA, Idarubicin, hoelzer chemotherapy regime, La La chemotherapy regime, ABVD, CEOP, 2-CdA, FLAG & IDA (with or without subsequent G-CSF treatment), VAD, M & P, C-Weekly, ABCM, MOPP and DHAP. A preferred chemotherapeutic regimen is CHOP.

The methods of the present invention may be used to treat a variety of B cell lymphomas but are particularly useful wherein said B cell lymphoma is non-Hodgkin's lymphoma (NHL). Rituximab has already been approved for the treatment of low-grade-follicular NHL, but the present inventors have surprisingly found that rituximab is also beneficial for the treatment of intermediate- and high-grade NHL, including bulky disease. Accordingly, the lymphomas which are treatable by the methods of the present invention include low grade/follicular non-Hodgkin's lymphoma (NHL), small lymphocytic (SL) NHL, intermediate grade/follicular NHL, intermediate grade diffuse NHL, chronic lymphocytic leukemia (CLL), high grade immunoblastic NHL, high grade lymphoblastic NHL, high grade small non-cleaved cell NHL, bulky disease NHL, mantle cell lymphoma, AIDS-related lymphoma and Waldenstrom's Macroglobulinemia, so long as such lymphomas are accompanied by bone marrow involvement which complicates the availability of radioimmunotherapy.

Also, the present invention may be used to treat autoimmune diseases. Examples thereof include glomerulonephritis, Goodpasture's syndrome, necrotizing vasculitis, lymphadenitis, periarteritis nodosa, systemic lupus erythematosis, arthritis, thrombocytopenia purpura, agranulocytosis, autoimmune hemolytic anemias, immune reactions against foreign antigens, myasthenia gravis, insulin-resistant diabetes, lupus (SLE and drug-induced lupus). Further, the present invention may be used to treat or prevent humoral immune responses against transplanted cells, tissues or organs.

Exemplary treatment conditions will now be illustrated by the following.

EXAMPLE 1

A patient with non-Hodgkin's is initially treated with RITUXAN®. This initial treatment comprises administration of 375 mg/m² RITUXAN® weekly for four weeks.

A week after this RITUXAN® antibody regimen is completed, the patient is then treated with a $^{90}Y$ radiolabeled humanized anti-CD22 antibody (humanized LL2 antibody disclosed in U.S. Pat. No. 5,789,554, to Leung et al, assigned to Immunomedics, incorporated by reference in its entire herein.) The patient is treated with a dosage of $^{90}Y$-labeled anti-CD22 antibody ranging from 10 to 30 mCi.

EXAMPLE 2

A patient who is to be transplanted with a kidney is treated prior to transplant with RITUXAN® at a dosage of 375 mg/m² weekly for four weeks in order to deplete B-cells prior to transplant and thereby reduce the likelihood of a humoral immune response against the transplanted organ.

Concurrent or within a week after RITUXAN® treatment, the subject is treated with low dosage of $^{90}Y$ radiolabeled humanized anti-CD22 monoclonal antibody, i.e., at a dosage of 10 to 30 mCi. The treated subject is then transplanted with the kidney by conventional surgical methods. Preferably, the subject will also be treated with anti-CD40L, anti-B7 or other immunosuppressants, e.g., cyclosporin.

What is claimed is:

1. A method of treating a subject having an autoimmune disease comprising the steps of:
   (i) administering a therapeutically effective amount of cold (non-radiolabeled) anti-CD20 monoclonal antibody having at least 20% of the B cell depleting activity of a C2B8 antibody; and
   (ii) administering a therapeutically effective amount of a hot (radiolabeled) anti-CD22 antibody or fragment thereof;
   wherein said anti-CD20 antibody and said radiolabeled anti-CD22 antibody or fragment are administered separately or in combination, and in either order.

2. The method of claim 1, wherein the amount of said cold anti-CD20 antibody ranges from 0.1 mg to 500 mg/m² per week.

3. The method of claim 2, wherein the amount of said cold anti-CD20 antibody is at least about 500 mg/m² weekly.

4. The method of claim 3, wherein said amount is about 375 mg/m² weekly for four weeks.

5. The method of claim 1, wherein said radio labeled anti-CD22 antibody or fragment is an yttrium-labeled anti-CD22 antibody or fragment.

6. The method of claim 2, wherein said radiolabeled anti-CD22 antibody fragment is a $Fab_2$, Fab, Fv, or domain deleted antibody.

7. The method of claim 5, wherein said anti-CD22 antibody is a $^{90}$Y labeled humanized LL2 antibody.

8. The method of claim 7, wherein the dosage of said radiolabeled antibody ranges from 10 to 30 mCi.

9. The method of claim 8, wherein said radiolabeled anti-CD22 antibody is administered about a week after a C2B8 antibody therapeutic regimen has been completed.

10. The method of claim 1 wherein the anti-CD20 antibody is C2B8.

11. The method of claim 1 wherein the autoimmune disease is a B cell related autoimmune disease.

12. The method of claim 1, wherein the cold (non-radiolabeled) anti-CD20 monoclonal antibody has at least 90% of the B cell depleting activity of a C2B8 antibody.

* * * * *

UNITED STATES PATENT AND TRADEMARK OFFICE
CERTIFICATE OF CORRECTION

PATENT NO.         : 6,846,476 B2
APPLICATION NO.    : 09/883962
DATED              : January 25, 2005
INVENTOR(S)        : Christine White Page 1 of 1

It is certified that error appears in the above-identified patent and that said Letters Patent is hereby corrected as shown below:

In Col. 1 at line 19, replace "cold anti-CD23 antibody" with "cold anti-CD20 antibody".

Signed and Sealed this

Nineteenth Day of May, 2009

JOHN DOLL
*Acting Director of the United States Patent and Trademark Office*